United States Patent [19]

The

[11] Patent Number: 5,171,887
[45] Date of Patent: Dec. 15, 1992

[54] PROCESS FOR THE PREPARATION OF OXALIC ACID AND SODIUM HYDROGEN OXALATE FROM CRUDE SODIUM OXALATE

[75] Inventor: Kwat I. The, Jonquiere, Canada

[73] Assignee: Alcan International Limited, Montreal, Canada

[21] Appl. No.: 827,895

[22] Filed: Jan. 30, 1992

Related U.S. Application Data

[63] Continuation of Ser. No. 520,664, May 8, 1990, abandoned.

[30] Foreign Application Priority Data

May 12, 1989 [CA] Canada ................................. 599561

[51] Int. Cl.$^5$ .............................................. C07C 55/06
[52] U.S. Cl. .................................................... 562/597
[58] Field of Search ................................. 562/593, 597

[56] References Cited

U.S. PATENT DOCUMENTS 3,377,369  4/1968  Sargent et al. ................... 562/593 X

FOREIGN PATENT DOCUMENTS 38-8709   6/1963  Japan ................................... 562/593
49-66621  6/1974  Japan ................................... 562/593

Primary Examiner—Arthur C. Prescott
Attorney, Agent, or Firm—Cooper & Dunham

[57] ABSTRACT

A process for producing oxalic acid, sodium oxalate or mixtures thereof comprises treating crude sodium oxalate solids or slurry, such as produced by the Bayer process in treating bauxite. The crude sodium oxalate solids or slurry include at least aluminum metal ions as well as other metal ions common to the Bayer process. The removal process comprises:

dissolving the crude sodium oxalate in an aqueous solution to form a solution of sodium oxalate;

separating insolubles from the solution;

passing the solution through an ion exchange column to convert sodium oxalate, the ion exchange column having a bed of cation exchange resin of the acidic type, the solution as it passes over the bed of resin exchanging sodium ions of the sodium oxalate with hydrogen ions of the resin to produce sodium hydrogen oxalate acid, oxalic acid or mixtures thereof depending upon the strength of acidity of the resin, the exchanged sodium ions and the Al metal ions remaining on the bed of resin; and recovering the sodium hydrogen oxalate, oxalic acid or mixtures thereof as the effluent solution from the ion exchange column.

17 Claims, 3 Drawing Sheets

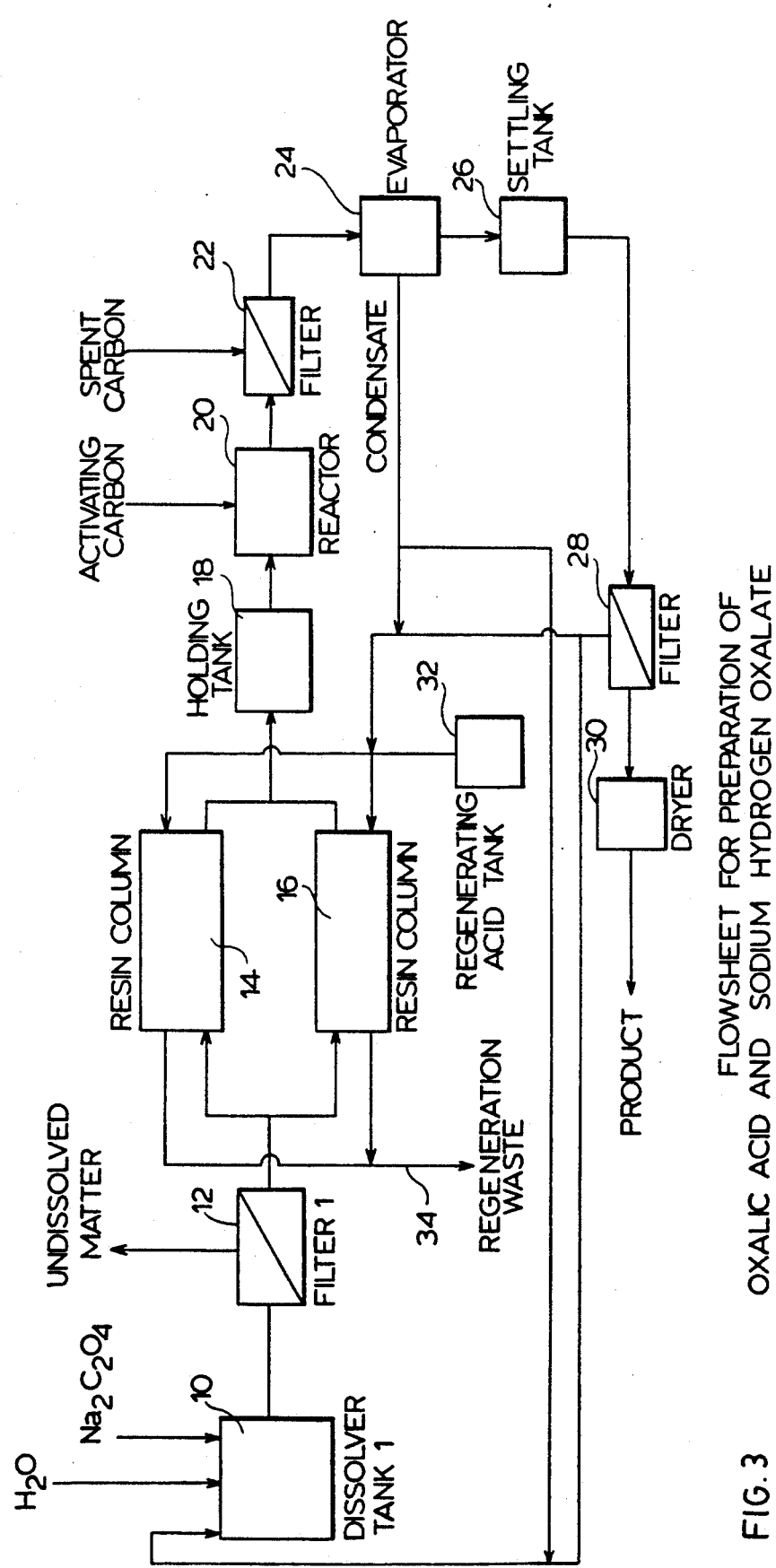
FIG. 3   FLOWSHEET FOR PREPARATION OF OXALIC ACID AND SODIUM HYDROGEN OXALATE

PROCESS FOR THE PREPARATION OF OXALIC ACID AND SODIUM HYDROGEN OXALATE FROM CRUDE SODIUM OXALATE

This is a continuation of application Ser. No. 07/520,664, filed May 8, 1990 now abandoned.

FIELD OF THE INVENTION

This invention relates the production of oxalic acid, sodium hydrogen oxalate or mixtures thereof by treating crude sodium oxalate solids or slurry such as derived from the Bayer process for treating bauxite in the manufacture of aluminum.

BACKGROUND OF THE INVENTION

In the well-known Bayer process, hot concentrated sodium hydroxide solution is used to attack Bauxite. The action of the sodium hydroxide solution is to solubilize alumina and thus separate it from the other oxides present in the mined bauxite. In the process of dissolving alumina with sodium hydroxide to form aluminates, organics in the bauxite are attacked and degraded into various compounds, such as the degradation of humic acids into oxalates and other organic moieties. The oxalates are soluble in the Bayer liquor. Over time, the recirculation of the Bayer liquor used in the processing of bauxite accumulates these impurities and when the concentration of the impurities reach their limits of supersaturation, they drop out of the solution as solids. A particular concern is with sodium oxalate which precipitates in the form of needles on the aluminum hydroxide seeds. These fine needles act as seeds for the precipitation of the aluminum hydroxide product, causing an increase of fine particles that have to be returned to the Bayer process for reprocessing. This significantly affects the overall efficiency of the Bayer process in isolating aluminum hydroxide from the bauxite.

The sodium oxalates are therefore undesirable and must be removed from the Bayer liquor when its concentration approaches the limit of supersaturation. The crude sodium oxalate is removed by evaporating t increase the sodium hydroxide concentration, which decreases the solubility of sodium oxalate, crystallizing the sodium oxalate, and removing the crystals by decantation, filtration and other techniques. The sodium oxalates are hazardous to the environment and the public, so that they cannot be readily discarded and must therefore be treated before release to the environment.

It is known that oxalic acid can be recovered from the crude sodium oxalate of the Bayer process by reacting the slurry containing the sodium oxalates with lime at 90° C. The reaction produces a calcium oxalate which is precipitated and readily separated from the slurry. The calcium oxalate can then be reacted with 96% sulfuric acid at elevated temperatures to produce a calcium sulfate byproduct and oxalic acid which can be recovered by crystallization of the oxalic acid from the solution. This technique is disclosed in Western German Patent Publication No. DE 2,553,870. This type of process, however, is complicated and consumes considerable lime, sulfuric acid, disposal of calcium sulfate byproduct, dangers in handling of concentrated sulfuric acid and is an energy intensive process. It is therefore desirable to develop a process for treating the crude sodium oxalates of the Bayer process, derive oxalic acid and sodium hydrogen oxalate from the oxalates of sufficient purity to be useful industrially.

Alternative techniques for treating of sodium oxalate, albeit for different purposes to upgrade technical grade sodium oxalate, is disclosed in USSR Patent 401131 issued May 5, 1976. The patent discloses an electrolysis process for upgrading technical grade sodium oxalate. The process is carried out in a fourchamber electrolytic cell where the chambers are separated by ion exchange membranes. In the process of electrolysis, the sodium ions of the sodium oxalate are exchanged for hydrogen ions to prepare oxalic acid of high purity. Iron cathode and graphite anode are used in establishing the electrochemical reaction.

Polish Patent 129059 issued Jun. 28, 1985 discloses a method of regenerating a cation exchanger used in the process of purifying technical grade sodium oxalate to prepare oxalic acid. The patent states that it is known to use a cation exchanger to convert sodium oxalate into sodium hydrogen oxalate and oxalic acid. To assist in the dissolution of the sodium oxalate in a hot solution, oxalic acid is included. The patent discloses the technique for regenerating the column used in preparing oxalic acid by the ion exchange treatment of the sodium oxalate. Such regeneration is carried out with a 7% nitric acid solution followed by a washing with demineralized water at 70° to 90° C. and a subsequent wash with water containing 2% to 5% of nitric acid.

SUMMARY OF THE INVENTION

According to an aspect of the invention, a process for producing oxalic acid, sodium hydrogen oxalate or mixtures thereof comprises treating crude sodium oxalate solids or slurry which is produced by the Bayer process in treating bauxite. The crude sodium oxalate solids or slurry include at least aluminum metals Al common to the Bayer process. The removal process comprises:

i) dissolving the crude sodium oxalate in an aqueous solution to form a solution containing sodium oxalate; and ii) passing the solution through an ion exchange column to convert sodium oxalate.

The ion exchange column has a bed of cation exchange resin of the acidic type. The solution, as it passes over the bed of resin, exchanges sodium ions of sodium oxalate with hydrogen ions of the resin to produce sodium hydrogen oxalate, oxalic acid or mixtures thereof depending upon the strength of acidity of the resin and said bed of resin removing the at least Al from said solution. The exchanged sodium ions and the Al metals remain on the bed of resin.

The sodium hydrogen oxalate, oxalic acid or mixtures thereof are recovered in the effluent solution from the ion exchange column.

Optionally, when solid oxalic acid and/or sodium hydrogen oxalate is desired, the effluent is evaporated, then cooled to crystallize out the product, which is then separated from the liquid.

BRIEF DESCRIPTION OF THE DRAWINGS

Preferred embodiments of the invention are shown in the drawings wherein:

FIG. 3 is a flowchart of the process for treating the crude sodium oxalate to produce oxalic acid.

DETAILED DESCRIPTION OF THE PREFERRED EMBODIMENTS

Figure 1:
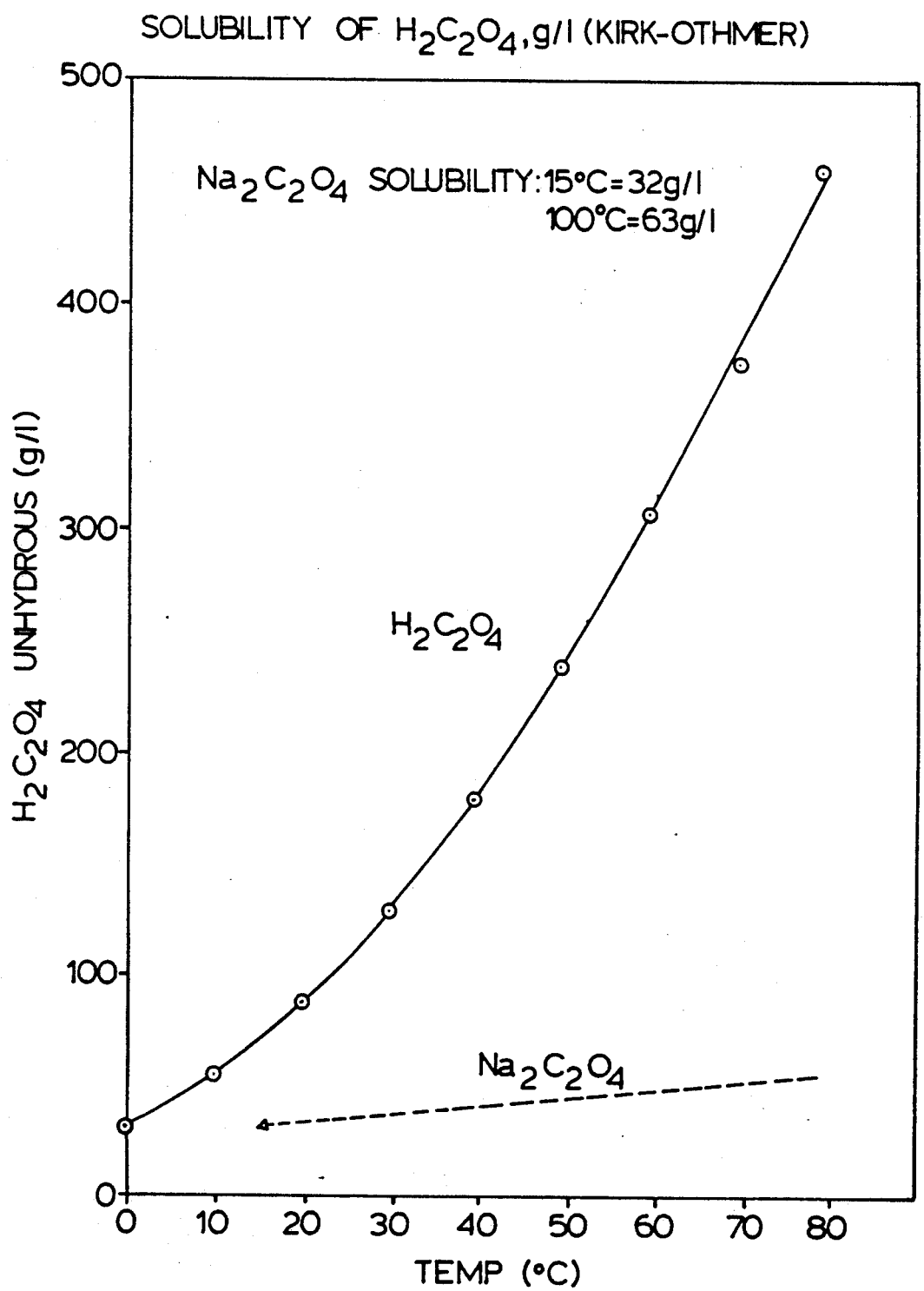
FIG. 1 is a graph showing the solubility of sodium oxalate and oxalic acid in water.

According to this invention, a process involving ion exchange resin is designed to treat waste crude sodium oxalate derived from the Bayer process to render the waste materials into industrially useful compounds of oxalic acid, sodium hydrogen oxalate or mixtures thereof while realizing the unexpected advantage of removing metallic impurities from the waste material and producing industrial grade oxalic acid. All of these features and advantages of the invention are attained in an economical process using readily available processing equipment. The process of this invention is capable of treating crude sodium oxalate, either derived from filter cake or slurry of the Bayer process and converting it into sodium hydrogen oxalate, oxalic acid or mixtures thereof depending upon the type of ion exchange resin used. The process is relatively simple, the product purity (oxalic acid) is acceptable, and the economics of the process are advantageous.

There are, of course, many references available which describe the classic Bayer process for treating bauxite to yield alumina. For a more complete understanding of the Bayer process, a description is provided in assignee's co-pending Canadian application Ser. No. 574,176 filed Aug. 9, 1988 which microbial degradation of oxalates.

In accordance with the process of this invention, an ion exchange resin is used to convert the sodium oxalate isolated from the crude sources of the Bayer process into sodium hydrogen oxalate, oxalic acid and mixtures thereof. The ion exchange process is the reversible interchange of ions between a solid and a liquid in which there is no permanent change in the structure of the solid resin bed. The ion exchange resin consists of inert chemical matrix with attached functional groups and mobile counter ions. The cation exchange resins fall into two broad groups; namely, strongly acidic and weakly acidic exchange resins. As is appreciated by those skilled in the art, the most common type of acidic exchanger is made of styrene-vinyldibenzene matrix and sulfonic acid functional groups. Other acidic exchangers consist of polyacrylic-vinyldibenzene and polystyrenedivinyldibenzene matrix resins with either carboxylic acid or sulfonic acid functional groups. Both carboxylic and sulfonic acid types of exchanger resins have strong affinity to cations, but have marked differences in their chemical behaviors.

The strong acid sulfonic resins remain ionized in acidic solutions and retain the ability to exchange cations in the solutions. The weaker carboxylic resins exist almost entirely in the free acid form in solutions of pH 4 or less, because the carboxylic acid is but slightly ionized. The counter cations are more tightly bound to the chemical matrix and are thus less mobile and available for exchange with the other cations. As a result depending upon the cation exchange resin used, the result of the ion exchange will vary. For general purposes in understanding the effects of the various types of resins, the reaction of the strongly acidic resin with sodium oxalate may be summarized by the following equations:

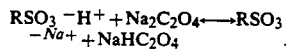
(1a)

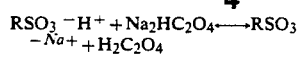
(1b)

The resin is strongly acidic and hence reacts readily with both sodium oxalate ($Na_2C_2O_4$) and sodium hydrogen oxalate ($NaHC_2O_4$). This is due to oxalic acid being weaker than the sulfonic acid, hence the reaction is driven towards the production of the oxalic acid.

When the weakly acidic resin is employed, the exchange is limited to the following reaction expressed in the equation:

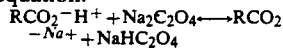
(2)

The ion exchange does not proceed to converting the sodium hydrogen oxalate into oxalic acid, because oxalic acid is relatively strong as the carboxylic acid and displaces the equilibrium of the process to the production of the sodium hydrogen oxalate of equation (2a).

With the process of this invention depending upon the acidic strength of the resin used, the products of the ion exchange will either be mixtures of sodium hydrogen oxalate and oxalic acid, when the strongly acidic resin is used, or sodium hydrogen oxalate when the weakly acidic resin is used.

Another common constituent of the crude sodium oxalate is sodium carbonate. With either the strongly acid or weakly acidic resins, the sodium carbonate is exchanged with a strongly acidic group as follows:

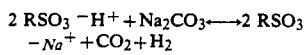
(3a)

and is exchanged with a weakly acidic group as follows:

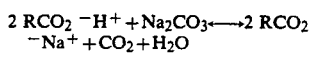

As is appreciated with the Bayer process, a variety of impurities, including metals, are dissolved by the Bayer process and hence found in the crude sodium oxalate as it exists in the filter cake, slurry or the like. The metal impurities may exist as hydroxides or other ionic forms. Examples of such impurities include not only aluminum (Al), but others such as calcium (Ca), iron (Fe), silicon (Si), vanadium (V) and arsenic (As) and the like. Quite surprisingly, it has been found that with the use of either the weak or strong acid exchange resins, these metal impurities are removed from the solution containing the sodium oxalate and retained on the exchange resin. This is quite significant in providing an effluent from the ion exchange column which is free of these metal impurities and improves the purity of the oxalic acid derived from the effluent. It is presumed that the metal impurities are exchanged on the resin with the hydrogen.

In the treatment, the crude sodium oxalate, in the form of a filter cake or slurry, is mixed with water to dissolve the sodium oxalate. The insolubles, if present, may be removed by some suitable separation, such as filtration. It is appreciated that insolubles may be left in the solution if they do not significantly reduce the effectiveness of the ion exchange column. The solution containing the dissolved sodium oxalates is then passed through the ion exchange column to convert the sodium oxalate into sodium hydrogen oxalate, oxalic acid or mixtures thereof, depending upon the type of resin used. The oxalic acid or sodium hydrogen oxalate or mixtures thereof are recovered in the solution which emerges from the ion exchange column as an effluent. The dissolved oxalic acid, sodium hydrogen oxalate, and mixtures thereof are useful industrially, and can be used without further treatment. By evaporating and cooling such effluent to cause the oxalic acid and/or sodium hydrogen oxalate to precipitate, the precipitated oxalic acid and/or sodium hydrogen oxalate can be removed from the effluent by filtration or other types of separating procedures. This optional separation of the sodium hydrogen oxalate and/or oxalic acid is useful when solid forms of these products are desired, such as to facilitate handling and shipping.

It has been realized that, in dissolving the crude sodium oxalate in an aqueous solution, dissolution is improved by dissolving the crude sodium oxalate in hot water. Furthermore, superior dissolution is obtained by including oxalic acid in the hot water before mixing with the crude sodium oxalate. It is believed that the dissolution of the sodium oxalate in a solution containing oxalic acid produces the chemical species of sodium oxalate, sodium hydrogen oxalate and oxalic acid due to the chemical reaction of sodium oxalate with oxalic acid. The relative concentrations present in the solution will depend on the amounts of each originally present and the amounts of sodium oxalate added. It is preferred that the temperature of the hot water containing oxalic acid in which the sodium oxalate is dissolved be in the range of 65° to 90° C. Although depending upon the circumstances, it is understood that the sodium oxalate is soluble in water at a temperature from a practical range of approximately 20° C, i.e., ambient, to approximately 90° C.

It is understood that the concentration of oxalic acid in the hot water to promote the dissolution of the sodium oxalate may vary considerably, the preferred concentration of the oxalic acid in the water is in the range of 30 to 60 grams per liter. In noting that the presence of oxalic acid enhances dissolution of the crude sodium oxalate, it is sometimes expedient to recirculate all or a portion of the effluent to the solution in which fresh crude sodium oxalate is dissolved. The recirculation of the effluent not only assists in dissolving the crude sodium oxalate, but in addition, sodium hydrogen oxalate which remains in the effluent is further converted to oxalic acid. As is demonstrated in the Examples section, such recirculation of the effluent can greatly enhance the concentration of oxalic acid in the effluent of the exchange column.

Figure 2:
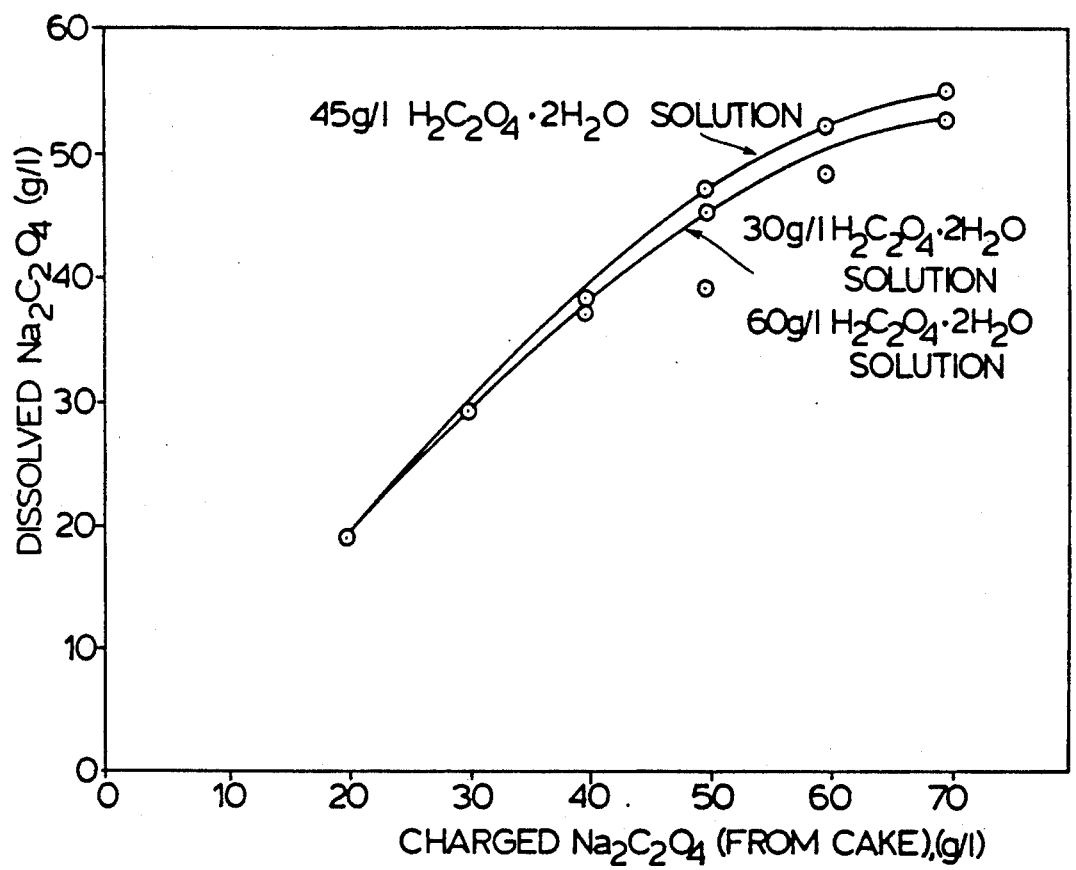
FIG. 2 is a graph showing the solubility of sodium oxalate in an aqueous solution containing oxalic acid.

As is apparent from FIG. 1, the solubility of oxalic acid in water is considerably greater than sodium oxalate. As low as 15° C, sodium oxalate has a solubility of approximately 32 grams per liter. As is apparent from FIG. 2, the presence of oxalic acid in the hot water in which the sodium oxalate is dissolved significantly increases the solubility due to the formation of other chemical moieties.

It is understood that with any type of ion exchange column, regeneration of the resin bed is required from time to time to replace the depletion of the hydrogen ions on the weakly or strongly acidic resin forms. Should the resin be of the strongly acidic type, the resin is represented by the formula: $RSO_3^-Na^+$ of equation (1b). Whereas with the weakly acidic, the resin is represented by the formula: $RCO_2^-Na^+$ of equation (2a). After exhaustion of the column, treatment of the resins with an excess of a dilute solution of strong mineral acid reverses the exchange reaction as demonstrated in the following equation providing the resin in the acid form.

The reactions with the strong or weak resins are as follows:

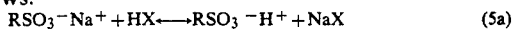  (5a)

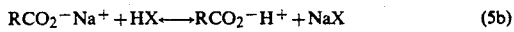  (5b)

In this manner, the resin bed is regenerated for reuse by way of a simple regeneration process.

With reference to FIG. 3, a flowchart for the preferred embodiment of the process of this invention is set out. The sodium oxalate is dissolved in tank 10 with the addition of water where the tank is, in accordance with this embodiment, heated by a suitable heating device to the desired temperature. The hot solution is passed through filter 12 to remove any undissolved matter. The hot solution is then passed through either resin column 14 or resin column 16 to effect the ion exchange. It is appreciated that the ion exchange process on the resin bed is equally effective for purposes of this invention regardless of whether the solution is cold or hot.

The effluent from either resin column 14 or 16 is transferred to a holding tank 18. The choice of the resin column 14 or 16 is dependent upon which column is in service and which column is in the regeneration mode in accordance with standard procedures in ion exchange technology. In this manner, down time is minimized with respect to treatment of incoming crude sodium oxalates. The effluent from the column as held in holding tank 18 is then treated in the reactor 20 with activated carbon to improve the clarity of the solution. The spent carbon is removed from the solution by way of filter 22, where the filter solution is passed on to evaporator 24. The evaporator 24 removes water to achieve precipitation or separation of the desired sodium hydrogen oxalate or oxalic acid which is passed on in solid form to a settling tank 26. The removed condensate is either passed to the tank 10 as shown, or used in rinsing of either of the resin columns. The product from the settling tank 26 is passed through a filter 28 to remove further solids where part of the liquid is used to displacement wash the resin column to recover the maximum amount of product retained in the column. The solids are then passed through a dryer 30 to provide the dried product in the form of either oxalic acid, sodium hydrogen oxalate or mixtures thereof.

The resin column 14 or 16 is regenerated by use of a strong mineral acid, such as sulfuric acid, as contained in tank 32. The acid in solution is passed through the respective resin column 14 or 16 during the regeneration mode and removed and disposed of in the regeneration waste line 34 in accordance with standard column regeneration techniques. The columns are washed with condensate from 24.

The following Examples demonstrate various preferred conditions in the operation of the process of this invention, but are understood not to be limiting with respect to the scope of the invention as defined in the accompanying set of claims.

EXAMPLE 1

Bayer sodium oxalate slurry (11.5 g, containing 52% $Na_2C_2O_4$) was added to a 500 mL beaker containing water (250 ml). The solution was heated on a hot plate for 15 minutes and the insoluble materials were filtered off (0.35 g, 3%). After cooling, the solution was passed through a column (8 mm diameter) containing strong acidic IR-120 Amberlite ® cation exchange resin in the acid form (50 g), at a rate of 200 to 300 mL hour. Activated carbon (about 0.5 g) was added to the effluent and the slurry was then heated to boil, and then filtered. The solution was evaporated to dryness under vacuum to yield pale yellow solid (3.7 g). The solid was identified as the oxalic acid anhydrous by X-ray diffraction ($\beta$ oxalic acid) and assayed by titration with $KMnO_4$ (95% purity). The yield of the crude product was thus 93% on the basis of the sodium oxalate content of the Bayer sodium oxalate slurry. Recrystallization of the solid in water resulted in a pure white colored oxalic acid crystal in needle form. They were identified as the oxalic acid dihydrate by X-ray diffraction analysis.

EXAMPLE 2

Bayer sodium oxalate slurry (6.2 g with 52.2% $Na_2C_2O_4$) was added to a beaker containing about 125 mL of water. After stirring for about 15 minute, the undissolved solid was separated by filtration and the filtrate was passed through a column ($\frac{3}{4}$" diameter) containing weakly acidic Amberlite IRC-50 ®(in the acid form, 50g), a rate of about 200 to 400 mL/hour. Activated carbon (about 0.4 g) was added to the effluent and the mixture was then heated to boil, and then filtered. The solution was then evaporated to dryness under vacuum to yield a pale yellow solid (3.27 g) identified as $NaHC_2O_4.H_2O$ by X-ray diffraction. The yield of the crude was 100%. Recrystallization of the solid in water gave a pure white colored sodium hydrogen oxalate monohydrate, $NaHC_2O_4.H_2O$ in 70% to 90% yield.

Bayer oxalate slurry (6.0 g with 52.5% $Na_2C_2O_4$) were similarly worked-up as above; but this time using another weakly acidic resin Amberlite IRC-718, ® (in the acid form, 50 g). The crude yield was 3.12 g, corresponding to 100%.

EXAMPLE 3

Crude sodium oxalate (115 g of cake containing 60 g of $Na_2C_2O_4$) were added to a stirred and heated (70° C.) solution of 60 g/l oxalic acid (945 mL). After 30 minutes at the temperature, the mixture was quickly filtered to remove undissolved solids (4.5 g $\approx$4%) and the filtrate, kept at 65° to 70° C., was passed through a heated (70° C.) jacketed column (17" with $\frac{3}{4}$" diameter) containing 552 g of strongly acidic Dowex-W-X8 ® resin in the hydrogen form, that had been filled with 220 mL (equivalent of the void volume) of 60 g/L oxalic acid solution. After all the sample solution had passed through the column, additional 220 mL of 60 g/L of oxalic acid were charged to the column to displacement wash out the sample solution completely. The combined solutions wee then evaporated to 500 mL after treatment with 1 g of activated carbon, and then cooled to room temperature (26° C). The oxalic acid crystals precipitated were filtered and dried in air and weighed (32.5 g).

EXAMPLE 4

The crude sodium oxalate was analyzed for impurities by inductively coupled plasma atomic emissions spectroscopy (ICPAES) technique. The solid products from the ion exchange treated sodium oxalate was analyzed for presence of the metal impurities. The metal impurities analyzed for, in both the crude material and the products, were aluminum, calcium, iron, silicon and vanadium. The results of these analyses are summarized in the following Table 1.

TABLE 1

METAL IMPURITIES FOUND IN CRUDE SODIUM OXALATE, OXALIC ACID AND SODIUM HYDROGEN OXALATE IN PERCENT

| ELEMENT IMPURITY | CRUDE SODIUM OXALATE % | OXALIC ACID FROM STRONGLY ACID RESIN % | SODIUM HYDROGEN OXALATE FROM WEAKLY ACIDID RESIN % |
|---|---|---|---|
| Al | 2.56 | 0.013 | 0.008 |
| Ca | 0.13 | 0.001 | 0.003 |
| Fe | 0.052 | 0.01 | 0.03 |
| Si | 0.047 | 0.007 | 0.003 |
| V | 0.010 | 0.0001 | 0.0001 |

It is apparent that regardless of use of strong or weakly acidic resins, the impurities are considerably reduced in the desired product which indicates that the metal ions are retained on the resin.

EXAMPLE 5

One litre of a solution of crude Bayer sodium oxalate filter cake containing 30 g/L $Na_2C_2O_4$, heated to 90° C., was passed through a 70 cm diameter 300 cm long water jacketed column maintained at about 90° C. containing 700 g of Dowex 50 W-X8 ® resin in the hydrogen form. The resulting effluent contained oxalic acid, at a concentration of 26.8 g/L. The resin was next treated with 500 mL of water, the effluent was called Wash Water; then treated with 500 mL of a 10% solution of sulfuric acid to regenerate the resin to the hydrogen form, the resulting effluent was called spent regenerant; followed by 500 mL of water to give an effluent called rinse water. This process was repeated four times in tests I, II, III, and IV, to yield four product effluents containing respectively 26.8, 52.4, 74.1 and 87.6 g/L oxalic acid. The concentration of oxalic acid in the effluents increased because the sodium hydrogen oxalate resulting from the reaction of $Na_2C_2O_4$ with the oxalic acid is more soluble than sodium oxalate, and this higher concentration was converted to the hydrogen form; i.e., the oxalic acid by the ion exchange resin.

From these three tests, the four sets of wash water, spent regenerant, and rinse water, were analyzed; the results are shown in Table 2. The results indicate that the Na, and the Al, Fe, Ca, Pb and As impurities are retained by the resin, and are not displaced by the wash water, but are removed from the resin by the regenerant solution of sulfuric acid, and that the remainder of these displaced cations are displacement washed out of the resin by the rinse water.

TABLE 2

ANALYSIS OF WASH WATER, SPENT REGENERANT AND RINSE WATER

| Test Sample | | Elements Present, in Parts per Million | | | | |
|---|---|---|---|---|---|---|
| | | Na | Al | Fe | Ca | Pb | As |
| I | Wash Water | | Not analyzed | | | | |
| | Spent Regenerant | 46000 | 230 | 0.008 | 9.4 | 0.5 | ND |
| | Rinse Water | 600 | 220 | 0.7 | 0.12 | 0.4 | ND |
| II | Wash Water | 5500 | 11 | 0.4 | 0.9 | 0.06 | ND |
| | Spent Regenerant | 43000 | 163 | 0.04 | 10.0 | 0.5 | ND |
| | Rinse Water | 1030 | 207 | 1.4 | 0.1 | 0.4 | ND |
| III | Wash Water | 5400 | 9 | 0.01 | 0.7 | 0.03 | ND |
| | Spent Regenerant | 43000 | 113 | 0.06 | 5.6 | 0.5 | ND |
| | Rinse Water | 766 | 172 | 1.5 | 0.05 | 0.3 | ND |
| IV | Wash Water | 7170 | 12 | 0.04 | 1.5 | 0.07 | ND |

TABLE 2-continued

ANALYSIS OF WASH WATER, SPENT REGENERANT AND RINSE WATER

| Test Sample | Elements Present, in Parts per Million | | | | | |
|---|---|---|---|---|---|---|
| | Na | Al | Fe | Ca | Pb | As |
| Spent Regenerant | 43000 | 125 | 0.4 | 8.2 | 0.5 | ND |

ND = Not Detected

EXAMPLE 6

A portion of the 87.6 g/L solution of oxalic acid obtained from Test III of Example 5 was evaporated to about 25% of its original volume to precipitate crystals of oxalic acid. Another portion of this same solution was passed through the ion exchange column in the hydrogen form for a second time. The resulting effluent was also evaporated to about 25% of its original volume to precipitate the oxalic acid. The solids were analyzed for their impurity contents; the results are shown in Table 3. These results show that both products have low concentrations of impurities, but that the sodium content of the product obtained on a single passage through the column is not high purity oxalic acid, since it contains about 35 % of sodium. However, on a second pass through the column, the sodium is replaced by hydrogen, and the sodium content of the resulting oxalic acid is only 0.038%, and the concentration of the other impurities is also reduced.

TABLE 3

| ANALYSIS OF OXALIC ACID PRODUCTS | | | | | | |
|---|---|---|---|---|---|---|
| Sample | Elements, in % | | | | | |
| | Na | Al | Fe | Ca | Pb | As |
| Precipitated 1 pass | 3.55 | 0.041 | 0.002 | 0.001 | 0.007 | N.D. |
| After 2nd Pass through Column | 0.038 | 0.027 | 0.001 | 0.001 | 0.002 | N.D. |

Although preferred embodiments of the invention have been described herein in detail, it will be understood by those skilled in the art that variations may be made thereto without departing from the spirit of the invention or the scope of the appended claims.

I CLAIM:

1. A process for producing oxalic acid, sodium hydrogen oxalate or mixtures thereof by treating crude sodium oxalate solids or slurry which is produced by the Bayer process in treating bauxite, said crude sodium oxalate solids or slurry include at least Al common to said Bayer process, said process comprises:
   i) dissolving said crude sodium oxalate in an aqueous solution to make a solution containing sodium oxalate;
   ii) passing said solution through an ion exchange column to convert sodium oxalate, said ion exchange column having a bed of cation exchange resin of an acidic type, said solution as it passes over said bed of resin exchanging sodium ions of said sodium oxalate with hydrogen ions of said resin to produce oxalic acid, sodium hydrogen oxalate or mixtures thereof depending upon the strength of acidity of said resin said bed of resin removing said at least Al from said solution, said exchanged sodium ions and said Al remaining on said bed of resin;
   iii) recovering said sodium hydrogen oxalate, oxalic acid or mixtures thereof as an effluent solution from said ion exchange column.

2. A process of claim 1, wherein said resin is of a weak acid type to convert said sodium oxalate to sodium hydrogen oxalate.

3. A process of claim 2, wherein said resin is a carboxylic acid type.

4. A process of claim 1, wherein said resin is of a strong acid type to convert said sodium oxalate to sodium hydrogen oxalate, oxalic acid or mixtures thereof.

5. A process of claim 4, wherein said resin is a sulfonic acid type.

6. A process of claim 1, wherein said solution of sodium oxalate is at a temperature in the range of 20° C. to 90° C., when passed through said ion exchange column.

7. A process of claim 6, wherein said solution is at a temperature in the range of 65° C. to 90° C.

8. A process of claim 7, wherein said step of dissolving said crude sodium oxalate in an aqueous solution includes use of oxalic acid in said aqueous solution to enhance the solubility of said crude sodium oxalate in said aqueous solution to form said sodium oxalate containing solution.

9. A process of claim 8, wherein said solution is at a temperature in the range of 20° C. to 90° C. when passed through said ion exchange column.

10. A process of claim 9, wherein said solution is at a temperature in the range of 65° C. to 90° C.

11. A process of claim 1, wherein said effluent is recirculated through said ion exchange column to improve purity of separated sodium hydrogen oxalate, oxalic acid or mixture thereof.

12. A process of claim 4, wherein said effluent containing sodium hydrogen oxalate and oxalic acid is recirculated to form a solution in which fresh crude sodium oxalate is dissolved in the presence of said oxalic acid, passing said solution containing recirculated sodium hydrogen oxalate through said ion exchange column to increase concentration of oxalic acid in said effluent.

13. A process of claim 1, wherein said impurities include in addition to Al, metals selected from the group consisting of Ca, Fe, Si, V, Pb and As, all of said metals being removed from said solution and retained on said bed of resin.

14. A process of claim , wherein any insolubles are separated from said solution before passing through said column.

15. A process of claim 1, wherein said solution of sodium oxalate is filtered to remove any insolubles before passing through said column.

16. A process of claim 1, wherein said effluent solution is concentrated to remove from said effluent sodium hydrogen oxalate, oxalic acid or mixtures thereof in solid form.

17. A process of claim 13, wherein said bed of resin is regenerated as needed to exchange hydrogen ions for said sodium ions and other metal ions.

* * * * *